(12) United States Patent
Luk et al.

(10) Patent No.: US 6,556,292 B2
(45) Date of Patent: Apr. 29, 2003

(54) HEAD SLAP CHARACTERIZATION USING OPTICAL SURFACE ANALYZER

(75) Inventors: Allan Kai Luk, Thornton, CO (US); Yue Ma, Longmont, CO (US)

(73) Assignee: Seagate Technology LLC, Scotts Valley, CA (US)

( * ) Notice: Subject to any disclaimer, the term of this patent is extended or adjusted under 35 U.S.C. 154(b) by 0 days.

(21) Appl. No.: 09/879,739

(22) Filed: Jun. 12, 2001

(65) Prior Publication Data

US 2002/0118358 A1 Aug. 29, 2002

Related U.S. Application Data

(60) Provisional application No. 60/271,293, filed on Feb. 23, 2001.

(51) Int. Cl.[7] .............................................. G01N 21/00
(52) U.S. Cl. .............................. 356/237.2; 356/237.3; 356/237.1
(58) Field of Search ......................... 356/237.1, 237.2, 356/237.3, 237.4, 237.5, 237.6, 394; 250/559.41, 559.42, 559.4, 559.45

(56) References Cited

U.S. PATENT DOCUMENTS

| 4,307,419 A | * 12/1981 | Matey et al. ............... 348/522 |
| 4,505,585 A | 3/1985 | Yoshikawa et al. ............. 21/32 |
| 4,789,238 A | 12/1988 | Ichikawa et al. ........... 356/237 |
| 5,875,029 A | 2/1999 | Jann et al. .................. 356/435 |
| 5,883,714 A | 3/1999 | Jann et al. .................. 356/349 |
| 5,898,492 A | 4/1999 | Imaino et al. ............... 356/237 |
| 5,898,499 A | 4/1999 | Pressesky .................... 356/357 |
| 5,969,370 A | 10/1999 | Imaino et al. ......... 250/559.06 |
| 6,046,801 A | 4/2000 | Liu et al. .................. 356/237.1 |
| 6,057,926 A | 5/2000 | Horai ......................... 356/430 |
| 6,078,385 A | 6/2000 | Yoshiyama et al. ...... 356/237.1 |
| 6,172,953 B1 | * 1/2001 | Kamiyama ............. 369/124.15 |

OTHER PUBLICATIONS

DCM–001 Rev. B, *Optical Surface Analyzer* User's Manual., authorized by Candela Instruments, Software Version 2.1.

\* cited by examiner

*Primary Examiner*—Hung Xuan Dang
*Assistant Examiner*—Tuyen Tra
(74) *Attorney, Agent, or Firm*—Merchant & Gould P.C.

(57) ABSTRACT

A system and method in which a commercial non-contact optical surface analyzer is utilized to characterize the severity of a head slap event through examination of the surface of a data storage disc. The optical surface analyzer selected has the capability of detecting surface topography using a high-resolution scanning head. When performing the analysis, the data storage disc may be removed from the disc drive and placed on a spindle. The data storage disc surface topography scan takes place while the disc is spinning. A full scan of the entire data storage disc surface can be done, as well as a zoomed scan on a specific area of the data storage disc surface, thereby allowing for a higher resolution scan on the surface encompassing a head slap event. Data captured by the optical surface analyzer can then be exported to a commercial mathematical program for analysis and presentation.

21 Claims, 5 Drawing Sheets

HEAD SLAP CHARACTERIZATION USING OPTICAL SURFACE ANALYZER

RELATED APPLICATIONS

This application claims priority of U.S. provisional application Serial No. 60/271,293, filed Feb. 23, 2001.

FIELD OF THE INVENTION

This application relates generally to the inspection of data storage disc surfaces and more particularly to a method and system for characterizing damage caused during a head slap event to a data storage disc surface using an optical surface analyzer.

BACKGROUND OF THE INVENTION

Disc drive reliability and performance have become increasingly important in today's technology marketplace. Original Equipment Manufacturers (OEMs), as well as end consumers, place high demands on disc drives, requiring the disc drives to function under a variety of environmental conditions and stresses.

During the installation and use of a disc drive, the disc drive may be subjected to a multitude of stresses. One such stress is a shock to the disc drive. OEMs routinely conduct and require that disc drives pass a battery of shock tests. Shock tests can include such tests as topple drop shock, non-operational shock, operational shock, etc. A disc drive is required to endure these shock tests and continue to perform to the customer's satisfaction. In addition, during product research and development stages, as well as during reliability testing, disc drive manufacturers routinely perform shock tests to ensure that current design and changes to the current design of the disc drive (e.g. actuator change, suspension change, slider process change, air-bearing surface design change, etc.) can meet or exceed shock test performance requirements.

One method of performing a shock test on a disc drive is termed "topple drop." During a topple drop shock test, a first edge of the disc drive is placed on a resting surface and a second edge of the disc drive is elevated to a specified angle above the resting surface. The second edge of the disc drive is then allowed to drop from this elevated height to the resting surface below, thereby causing a shock to the disc drive. Topple drop shock tests can include drops from such angles as 60, 75, and 110 degrees. Topple drop shock tests may be performed while the disc drive is operational or while the disc drive is non-operational (i.e. the data storage disc may not be spinning and the heads may be in the parked position).

One of the failure modes in shock-induced stress testing such as topple drop is head slap. Head slap is a phenomenon in which a disc drive head, which is mounted on an actuator arm positioned within the disc drive, comes into contact with the magnetic recording media of the data storage disc. During normal operation, the head is mounted on the actuator arm so that the head can read the information stored on the magnetic recording media of the data storage disc. The head includes an air-bearing slider that allows the head to fly in close proximity, approximately 1 micro inch, above the surface of the data storage disc without actually contacting the surface. When a head slap event occurs, the head is caused to come into contact with the magnetic recording media of the disc drive. A head slap event can typically occur during a shock test such as topple drop because the motion created by the shock can cause the actuator arm on which the head is mounted to pivot, thereby causing the head to contact the magnetic recording media one or more times.

A head slap event is detrimental to a data storage disc because it can lead to mechanical damage to the head and magnetic recording media surface. Damage caused during a head slap event can also create debris from the destruction to the head and magnetic recording media surface that can become trapped underneath the air-bearing surface of the head. Particles trapped in this position while the disc drive is spinning can lead to deep scratches on the datastorage disc surface as well as a head crash.

One of the preferred methods to understand shock test performance in a disc drive is to analyze the severity of the damage caused during a head slap event to the magnetic recording media of the data storage disc surface. In general, if the damage caused to the surface is severe, it can be assumed that the slapping motion produced by the actuator arm and head is also severe and that damage to the head itself will be severe. As a result, the greater the severity of damage caused during the head slap event, the greater the chance that the disc drive will fail a shock test. Therefore, the ability to characterize the severity of the damage caused during a head slap event is very critical to the prediction of overall reliability of the disc drive from both a design and cost point of view.

A current method used to analyze a head slap event requires disassembly of the disc drive and placement of the data storage disc under an optical microscope for both low and high magnification surface scan analysis. Although this method can provide qualitative information on the severity of the head slap event, a disadvantage is that the results are crude, involving only a two-dimensional analysis of the data storage disc surface. Further, such an analysis is very subjective, requiring the operator conducting the analysis to make a determination as to the severity of damage to the surface using only this two-dimensional representation of the damage caused to the surface during the head slap event. Because different operators use different standards when evaluating and ranking the severity of a head slap event, significant variations in the analysis of the severity of a head slap event can occur. Finally, an analysis using an optical microscope can vary depending on microscope settings and lighting conditions.

Another method employed to analyze the severity of a head slap event is through the use of a contact profilometer. The contact profilometer includes a stylus that contacts and traces the surface of the data storage disc and thereby measures any imperfections on the data storage disc's surface. While this method can provide an accurate measurement of the surface damage, the process is slow, requiring a significant amount of time to characterize the damage depth of an entire head slap event region on a data storage disc. In addition, the stylus on the contact profilometer can potentially scratch the surface of the data storage disc as it traces the surface during analysis, thereby causing additional damage to the surface.

Accordingly there is a need for a system and method that can provide both accurate and efficient characterization of the severity of a head slap event.

SUMMARY OF THE INVENTION

Against this backdrop the present invention has been developed. A system and method have been created in which a commercial non-contact optical surface analyzer is utilized to characterize the severity of a head slap event through examination of the surface of a data storage disc. The optical surface analyzer selected has the capability of detecting surface topography using a high-resolution scanning head. When performing the analysis, the data storage disc may be removed from the disc drive and placed on a spindle of the optical surface analyzer. The scanning of the data storage disc surface topography takes place while the disc is spinning. A full scan of the entire data storage disc surface can be done, as well as a zoomed scan on a specific area of the data storage disc surface, thereby allowing for a higher resolution scan on the surface encompassing a head slap event. Data captured by the optical surface analyzer can then be exported to a commercial mathematical program for analysis and presentation.

There are several advantages to this system and method. First, the system and method are relatively fast and efficient, requiring less than one minute for a full data storage disc surface scan and approximately 45 seconds for a zoomed scan. Second, the optical surface analyzer equipment is capable of a sub-angstrom sized vertical resolution and a sub-micron sized lateral resolution scan range. This allows for higher resolution and a three-dimensional qualitative analysis of the head slap event area. Further, the data collected by the optical surface analyzer can allow for a quantitative analysis to be performed. Third, use of the optical surface analyzer does not involve physical contact with the surface of the data storage disc, thereby preventing potential damage to the data storage disc surface during analysis.

These and various other features as well as advantages which characterize embodiments of the present invention will be apparent from a reading of the following detailed description and a review of the associated drawings.

DETAILED DESCRIPTION

Figure 1:
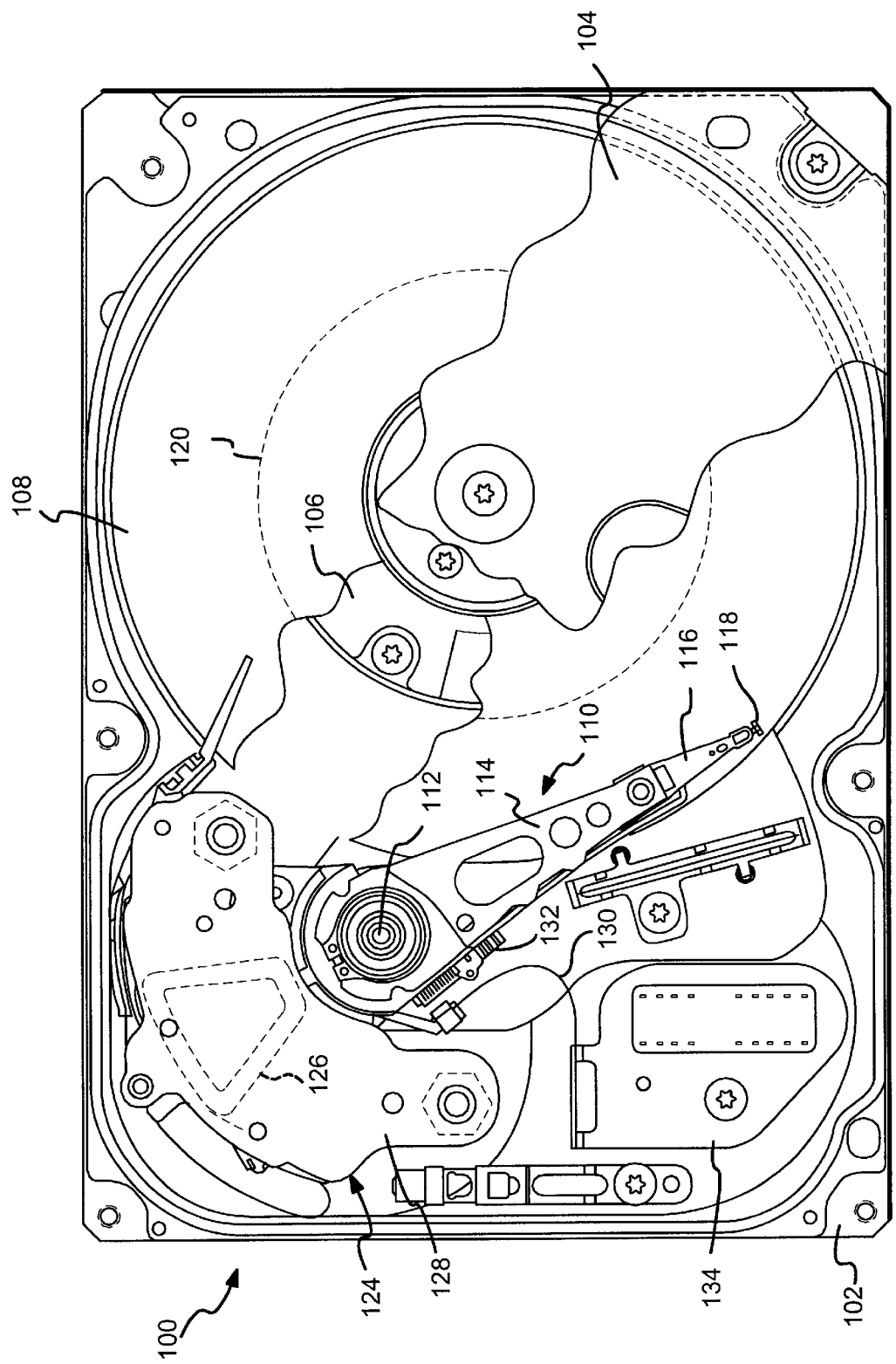
FIG. 1 is a plan view of a disc drive incorporating an example embodiment of the present invention showing the primary internal components of the disc drive.

A disc drive 100 constructed in accordance with a preferred embodiment of the present invention is shown in FIG. 1. The disc drive 100 includes a base 102 to which various components of the disc drive 100 are mounted. A top cover 104, shown partially cut away, cooperates with the base 102 to form an internal, sealed environment for the disc drive in a conventional manner. The components include a spindle motor 106 that rotates one or more data storage discs 108 at a constant high speed. Information is written to and read from tracks on the discs 108 through the use of an actuator assembly 110, which rotates during a seek operation about a bearing shaft assembly 112 positioned adjacent the discs 108. The actuator assembly 110 includes a plurality of actuator arms 114 which extend towards the discs 108, with one or more flexures 116 extending from each of the actuator arms 114. Mounted at the distal end of each of the flexures 116 is a head 118 that includes an air bearing slider enabling the head 118 to fly in close proximity above the corresponding surface of the associated disc 108.

During a seek operation, the track position of the heads 118 is controlled through the use of a voice coil motor (VCM) 124, which typically includes a coil 126 attached to the actuator assembly 110, as well as one or more permanent magnets 128 which establish a magnetic field in which the coil 126 is immersed. The controlled application of current to the coil 126 causes magnetic interaction between the permanent magnets 128 and the coil 126 so that the coil 126 moves in accordance with the well-known Lorentz relationship. As the coil 126 moves, the actuator assembly 110 pivots about the bearing shaft assembly 112, and the heads 118 are caused to move across the surfaces of the discs 108.

The spindle motor 116 is typically de-energized when the disc drive 100 is not in use for extended periods of time. The heads 118 are moved over park zones 120 near the inner diameter of the discs 108 when the drive motor is de-energized. The heads 118 are secured over the park zones 120 through the use of an actuator latch arrangement, which prevents inadvertent rotation of the actuator assembly 110 when the heads are parked.

A flex assembly 130 provides the requisite electrical connection paths for the actuator assembly 110 while allowing pivotal movement of the actuator assembly 110 during operation. The flex assembly includes a printed circuit board 132 to which head wires (not shown) are connected; the head wires being routed along the actuator arms 114 and the flexures 116 to the heads 118. The printed circuit board 132 typically includes circuitry for controlling the write currents applied to the heads 118 during a write operation and a preamplifier for amplifying read signals generated by the heads 118 during a read operation. The flex assembly terminates at a flex bracket 134 for communication through the base deck 102 to a disc drive printed circuit board (not shown) mounted to the bottom side of the disc drive 100.

A head slap event, as described above, may occur whenever one or more of the heads 118 contact the surface of one or more of the discs 108, possibly causing damage to both the heads and disc surfaces. It is therefore advantageous when designing a disc drive such as disc drive 100 to be able to characterize the damage caused to the surfaces of the data storage discs during a head slap event. A system and method for such characterization are described below.

Figure 2:
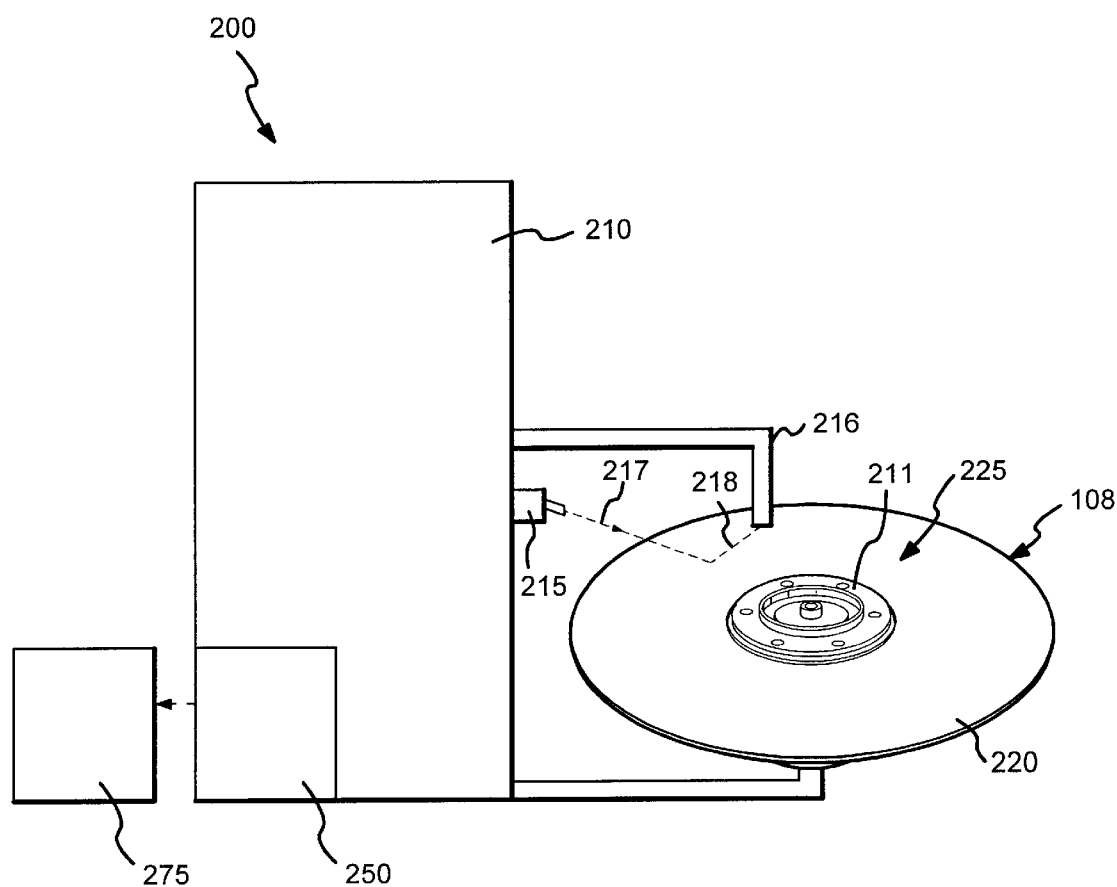
FIG. 2 is a simplified schematic view of an optical surface analyzer system in accordance with an exemplary embodiment of the present invention.

An optical surface analyzer system 200 is illustrated in FIG. 2 according to an exemplary embodiment of the invention. The system 200 includes an optical analyzer 210, a disc drive spindle 211, a laser beam emitter 215, and a light sensor 216. A data storage disc 108 has data storage disc surface 225 carrying a magnetic recording media 220. The data storage disc 108 is coupled to the spindle 211. The spindle 211 can be spun, thereby causing the disc 108 to spin. A laser beam 217 consisting of polarized light is emitted from laser beam emitter 215. This laser beam 217 is directed at surface 225 of the data storage disc 108. Reflected light 218 reflected by the data storage disc surface 225 is sensed by sensor 216 that detects changes in polarization of the reflected light 218. These changes are related to changes in the topography of the surface 225 of the data storage disc 108. As the data storage disc 108 is spun, the emitter 215 and/or the sensor 216 are positioned over each track of the spinning surface 225 of the data storage disc 108. A data storage module 250 records the data detected by the sensor 216. In this manner, the entire surface 225 of the data storage disc 108 can be scanned and recorded.

In one example embodiment according to the invention, the optical surface analyzer system 200 utilized is a model OSA 5100 Optical Surface Analyzer manufactured by Candela Instruments located in Fremont, Calif. The Candela Instruments Analyzer is listed by way of example only, and other such optical surface analyzer systems which provide similar scanning resolution in three-dimensions may also be used without departing from the scope of the invention.

The data retained in the data storage module 250 of the optical surface analyzer can be exported to a processing module 275. The processing module 275 may consist of one or more commercial mathematical systems that are adapted to further manipulate the data and generate one or more three-dimensional visual representations of the data storage disc surface based on the data. In an example embodiment according to the invention, the commercial mathematical system MatLab version 5.3, created by The Mathworks of Natick, Mass., is utilized to process the data from the data storage module 250 and create one or more three-dimensional representations of the data, such as those shown in FIGS. 4–6. Other commercial mathematical systems may also be used to manipulate and present the data exported from the optical surface analyzer system 200.

It should be understood that the configuration of the optical surface analyzer system 200 as illustrated in FIG. 2 is by way of example only, and other configurations may be used. For example, more than one emitter 215 and sensor 216 may be used so as to further speed up the disc scanning process. Also, the processing module 275 may be implemented as an integral component of system 200, or may be a stand-alone component. Other such modifications may also be made to the optical surface analyzer system 200 without departing from the spirit of the invention.

Figure 3:
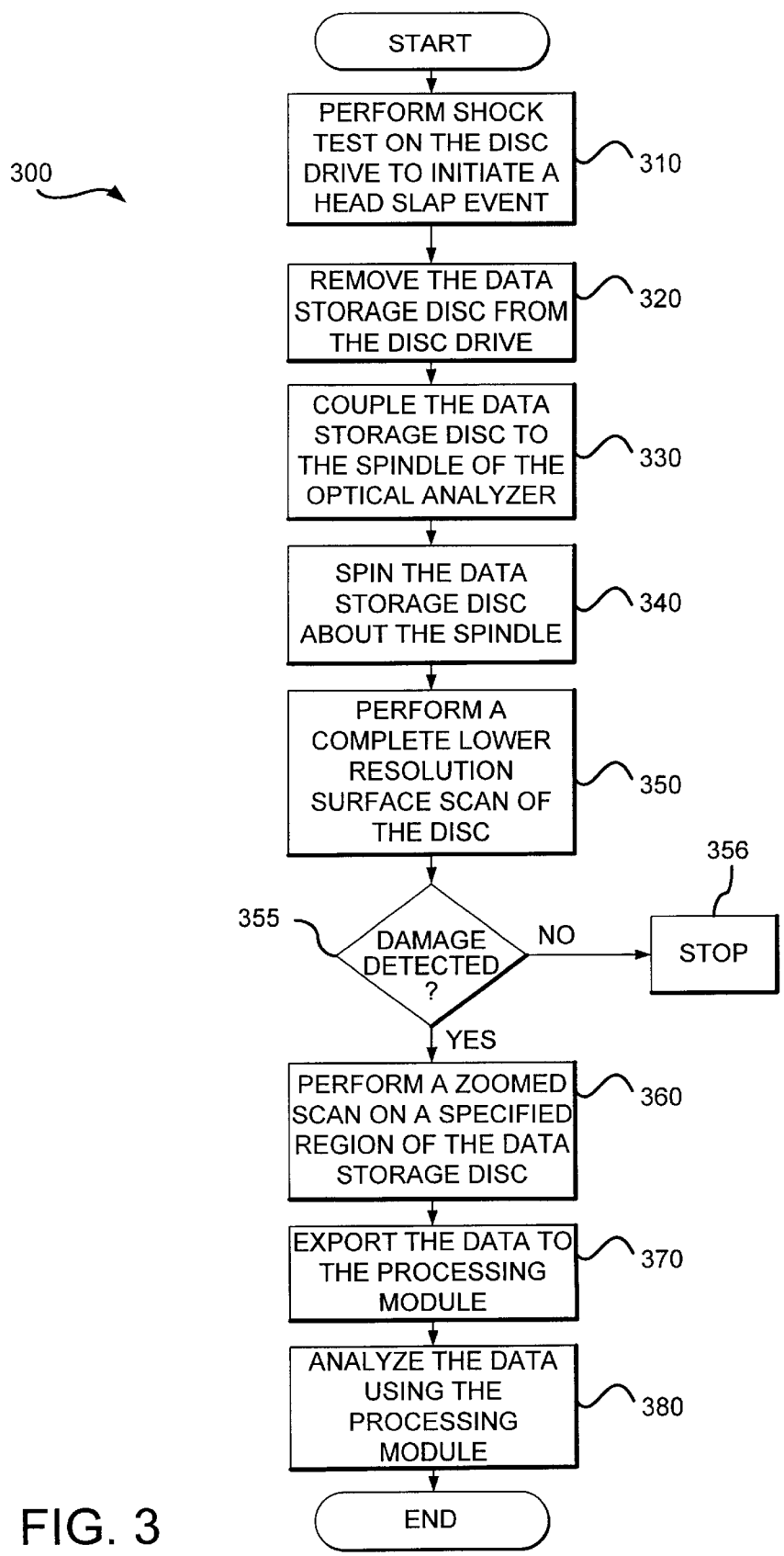
FIG. 3 is a flow chart of the method of characterization of a head slap event employed in accordance with an example embodiment of the present invention.

A method 300 for using an optical surface analyzer system such as 200 is shown in FIG. 3. In operation module 310, a shock test is performed on the disc drive 100 such as the topple drop test described above. The shock test should preferably be conducted so that a head slap event is induced. Next, once the shock test has been performed, in operation module 320 the data storage disc 108 is removed from the disc drive 100. Then, in operation module 330 the data storage disc is coupled to the optical analyzer on the optical analyzer spindle 211.

In operation module 340, the spindle 211 and the data storage disc 108 mounted on the spindle are spun at a specified rate of speed. The speed at which the spindle and data storage disc are to be spun is dependent on the specifications provided with the optical analyzer. Once the data storage disc 108 has reached the specified spinning speed, a complete lower resolution surface scan using polarized light is performed in operation module 350. The complete lower resolution surface scan in module 350 is performed so as to provide a detailed view of the entire data storage disc surface.

Once the complete lower resolution surface scan has been done, control transfers to query operation module 355. Control transfers to module 360 where it is possible to conduct a zoomed scan if damage is detected in query operation module 355. The zoomed scan in module 360 involves focusing the optical analyzer on a specified region of the surface of the data storage disc. Typically, this specified region of the data storage disc can include an area comprising damage caused during one or more head slap events. The zoomed scan of module 360 can be conducted at a higher resolution so as to provide greater detail with regard to the damage caused during the head slap event. If no damage is detected in module 355, control transfers to module 356 where the process is stopped because no head slap damage exists.

During and/or after the optical analyzer has completed scanning the surface of the data storage disc 108, the data collected by the optical analyzer is exported in operation module 370 to the processing module 275. The data exported in operation module 370 may be in the format of a text file or other binary or proprietary format that the processing module can interpret. Exportation may not be necessary if the optical analyzer contains the necessary software and hardware for data analysis.

Finally, in operation module 380 the processing module 275 may be used to analyze the data exported by the optical analyzer. The data may be analyzed both qualitatively (e.g. visual examination and comparison of the damage to other head slap events) as well as quantitatively (e.g. statistical analysis of the damage). This analysis may include manipulation of the data for statistical analysis as well as three-dimensional modeling of the data to illustrate the magnitude, volume, and topography of the head slap event. For example, in the exemplary embodiment shown, the user may conduct a visual qualitative examination of the three-dimensional modeling of the data. Further, the commercial analytical software may be used to quantitatively measure a damage volume for a head slap event, and this damage volume may be compared to the damage volume associated with other head slaps. Other statistical analysis may also be done, such as the use of pattern recognition software to filter out noise and identify the total damage caused during the head slap event. One skilled in the art should understand that various other methods of qualitative and quantitative analysis may also be used to manipulate and analyze the data collected by the optical analyzer.

It should be understood that the method 300 described above is by way of example only, and modifications to the method may be made without departing from the invention. For example, it may be unnecessary to perform the shock test described in module 310 if a disc drive is provided that has already undergone a head slap event, such as when a disc drive is returned by an OEM for analysis. In this case, operation module 310 may be bypassed. Further, the processing module 275 described in operation modules 370 and 380 may be implemented as part of the optical analyzer functions itself, thereby making the exportation of data provided in module 370 unnecessary. Other modifications to the method 300 may also be made.

Figure 4:
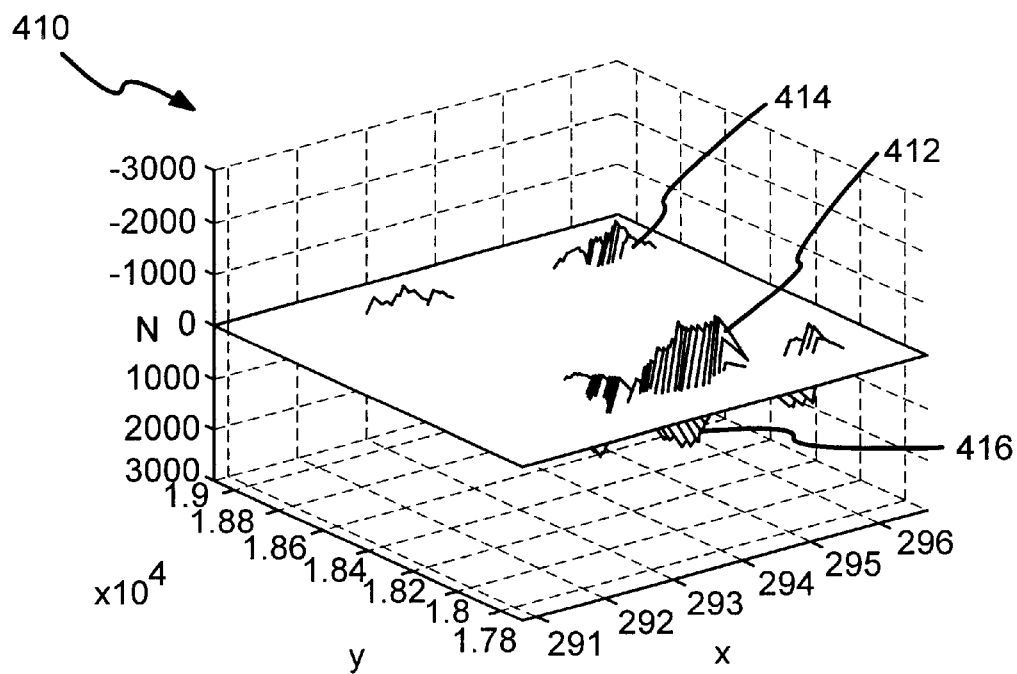
FIGS. 4–6 are three-dimensional visual representations of a head slap event in accordance with an example embodiment of the present invention.
Figure 5:
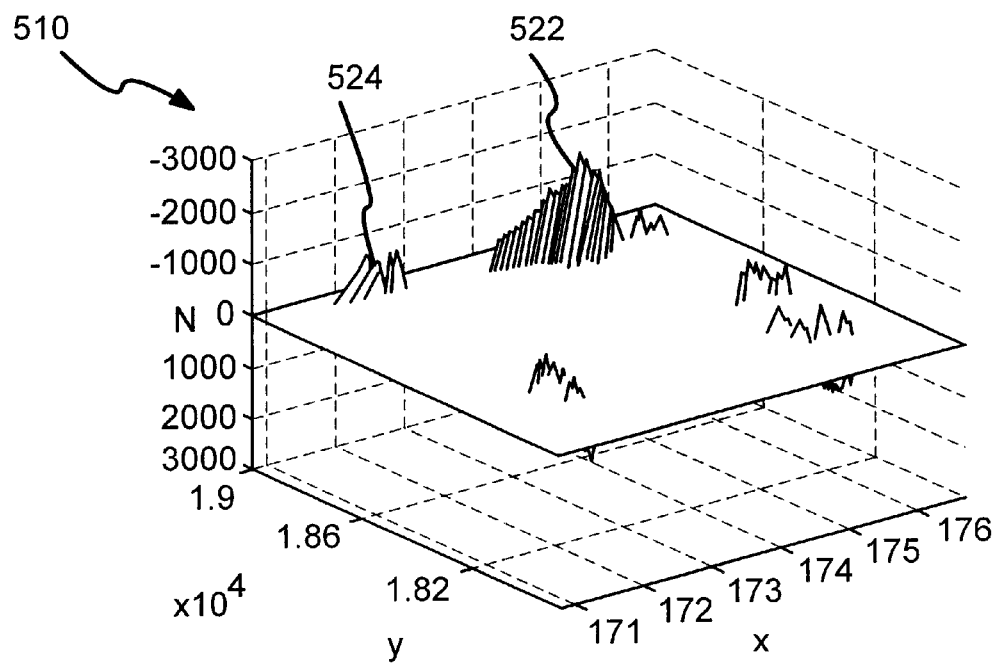
Figure 6:
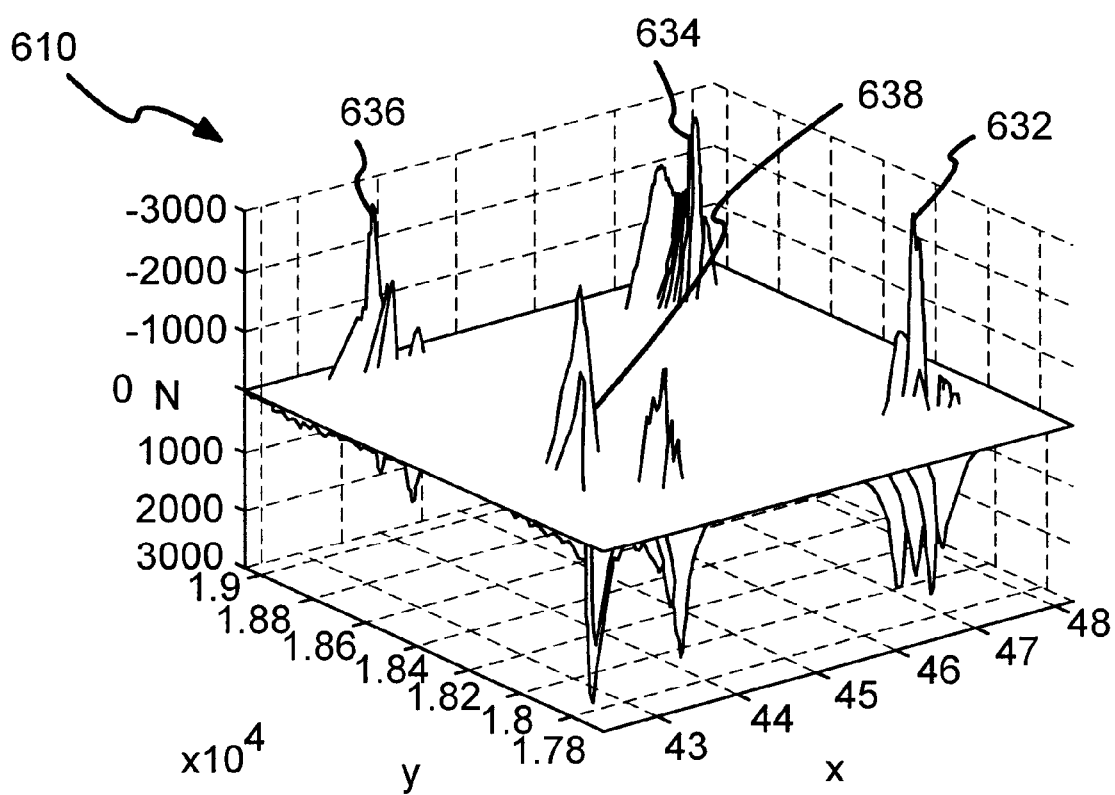

An example of the analysis that maybe conducted by the processing module 380 is shown in FIGS. 4–6. The FIGS. 4–6 are three-dimensional surface plots created from the data exported by the optical analyzer. In FIG. 4, the three-dimensional visual representation 410 illustrates the surface topography of a region of a data storage disc that has suffered head slap damage caused during a 60-degree topple drop shock test. The topple drop shock test in this example embodiment was performed while the disc drive was non-operational. However, one skilled in the art should understand that the topple drop shock test may be performed while the drive is operational. Further, other shock tests may also be performed so as to cause a head slap event.

The spikes 412, 414 on the plot in FIG. 4 may represent where a corner of the head came into contact with the surface of the data storage disc. The deformation 416 extending in the opposite direction may represent a rising of the data storage disc surface due to the damage caused during the head slap event. Similarly, spikes 522 and 524 of visual representation 510 shown in FIG. 5 represent contact between the head and the data storage disc surface during a 75-degree topple drop shock test. Finally, in FIG. 6, spikes 632, 634, 636, and 638 of visual representation 610 show head slap damage caused during a 110-degree topple drop shock test. The three-dimensional representations shown in FIGS. 4–6 should be understood to be examples only, and other methods for analysis of the data created by the optical analyzer can be conducted. For example, a quantitative analysis of the data points themselves can be done by manually manipulating the data using a typical spreadsheet or other such analysis device.

In the example embodiment, the three-dimensional plots of FIGS. 4–6 may be utilized by the user to conduct a visual qualitative analysis of the head slap event. Through examination of the plots, the user may discern generally how much damage was caused, and the user may also determine which portion of the head 118 contacted the surface of the data storage disc 108 first and therefore caused the most damage. The user may make this determination by examining the damage so as to locate the largest footprint or most severe damage. This area should represent where the head 118 first contacted the surface 225, because subsequent contacts with the surface should decrease in energy and therefore create a smaller footprint or less damage. From the location of this most severe damage, the user may be able to discern which portion of the head or actuator arm first contacted the surface of the data storage disc. This type of information may be valuable for design and implementation of the head and actuator arms.

There are several advantages to the system 200 and method 300 described above. First, the speed at which the surface analyzer 210 scans of the surface of the data storage disc is very fast relative to previous systems. The data storage disc 108 can be spun at speeds approximating 10,000 RPM or more. A complete lower resolution surface scan as described in operation module 350 can be finished in less than one minute, and the zoomed scan in operation module 360 can be done in less than 45 seconds. Because of the speed of the scanning process, additional head slap events may be analyzed in a shorter period of time, thereby providing more data to aid in a better understanding of head slap event characteristics.

Second, the optical analyzer 210 scans at a very high (sub-angstrom sized vertical and sub-micron sized lateral) resolution, and the data created by the optical analyzer 210 can be analyzed three-dimensionally. This three-dimensional analysis can provide greater insight into the characteristics of the head slap event, including the size and shape. Also, because the optical analyzer provides a plurality of data points, the analysis can be conducted quantitatively through analysis of the data points themselves as well as qualitatively through analysis of one or more visual representations created using the plurality of data points. Further, through analysis of the three-dimensional representations of the head slap event, such determinations as which portion of the actuator arm actually contacted the magnetic recording media of the data storage disc can be made. These types of determinations may allow for the redesign of the components on the actuator arm as well as the material comprising the surface of the data storage disc so as to minimize damage caused during a head slap event.

Third, the method employed by the optical analyzer 210 does not involve physical contact with the surface of the data storage disc during analysis of the surface. Because of this non-contact method, no further damage will be caused to the surface of the data storage disc during surface analysis.

In summary, an embodiment of the invention may be viewed as a method of detecting damage to a magnetic recording media (for example 220) on a data storage disc (for example 108) caused by a head slap event in a disc drive (for example 100). The method may comprise the steps of: spinning a data storage disc (for example 108); scanning a surface (for example 225) of the spinning data storage disc (for example 108) using an optical analyzer laser beam (for example 217); sensing changes in a reflected light beam (for example 218) created by the laser beam (for example 217) reflecting from the surface (for example 225) of the spinning data storage disc (for example 108); acquiring a plurality of data points corresponding to the changes in the reflected light beam (for example 218); and characterizing the damage caused during the head slap event to the magnetic recording media (for example 220) on the surface (for example 225) of the spinning data storage disc (for example 108) based on the plurality of data points.

In another embodiment according to the invention, a system (for example 200) for characterizing damage caused to a magnetic recording media (for example 220) on a surface (for example 225) of a data storage disc (for example 108) during a head slap event may comprise an optical analyzer module (for example 210), a data storage module (for example 250), and a processing module (for example 275). The optical analyzer module (for example 210) may comprise a spindle (for example 211), wherein the data storage disc (for example 108) is coupled to and spun on the spindle (for example 211), at least one laser beam (for example 217) directed at the surface (for example 225) of the data storage disc (for example 108), and at least one sensor (for example 216) operable to receive reflected light (for example 218) from the at least one laser beam (for example 217) reflecting from the surface (for example 225) of the data storage disc (for example 108) and sense changes in a direction of the reflected light (for example 218). The data storage module (for example 250) may be operably coupled to the analyzer module (for example 210) for storing a plurality of data points generated by the optical analyzer (for example 210), the plurality of data points quantifying the changes in the direction of the at least one light beam (for example 217). The processing module (for example 275) may be coupled to the optical analyzer module (for example 210) and the data storage module (for example 250) and may be operable to manipulate the plurality of data points to qualitatively and quantitatively represent the damage caused during the head slap event to the magnetic recording media (for example 220) on the surface (for example 225) of the data storage disc (for example 108).

In another example embodiment according to the invention, a disc damage analyzer (for example 200) may comprise an optical analyzer (for example 210) having a laser beam (for example 217) operably directed toward a magnetic recording media (for example 220) on a data storage disc (for example 108) and having a sensor (for example 216) to receive a plurality of light data points associated with reflected light (for example 218) from the laser beam (for example 217) reflecting from the surface (for example 225) of the data storage disc (for example 108) and a means (for example 275) for qualitatively and quantitatively characterizing the plurality of light data points to indicate damage caused by a head slap event.

It will be clear that the present invention is well adapted to attain the ends and advantages mentioned as well as those inherent therein. While an exemplary embodiment has been described for purposes of this disclosure, various changes and modifications may be made which are well within the scope of the present invention. For example, it may be unnecessary to disassemble the disc drive and remove the data storage disc in order to perform the optical surface scan.

Instead, the scan of the surface of the data storage disc could possibly be conducted through one or more viewing windows located on the top cover of the disc drive, thereby eliminating the need to destroy the disc drive through disassembly. Numerous other changes may be made which will readily suggest themselves to those skilled in the art and which are encompassed in the spirit of the invention disclosed and as defined in the appended claims.

What is claimed is:

1. A method of detecting damage to a magnetic recording media on a data storage disc caused by a head slap event in a disc drive, the method comprising steps of:
   (a) spinning the data storage disc;
   (b) scanning a surface of the spinning data storage disc using an optical analyzer laser beam;
   (c) sensing changes in a reflected light beam created by the laser beam reflecting from the surface of the spinning data storage disc;
   (d) acquiring a plurality of data points corresponding to the changes in the reflected light beam; and
   (e) characterizing the damage caused by the head slap event to the magnetic recording media on the surface of the spinning data storage disc based on the plurality of data points.

2. The method according to claim 1 wherein the characterizing step comprises steps of:
   (e)(i) performing a qualitative analysis of the plurality of data points; and
   (e)(ii) performing a quantitative analysis of the plurality of data points.

3. The method of claim 2, wherein the characterizing step (e) further comprises a step of (e)(iii) plotting a three-dimensional representation of the plurality of data points.

4. The method of claim 2, wherein the characterizing step (e) further comprises a step of (e)(iii) determining a portion of a slider carried by an actuator arm that caused the damage to the surface of the spinning data storage disc from the qualitative and quantitative analyses.

5. The method of claim 1, wherein the sensing step (c) further comprises steps of:
   (c)(i) selecting an area on the surface of the spinning data storage disc;
   (c)(ii) zooming in on the area using the optical analyzer; and
   (c)(iii) focusing the optical analyzer on the area.

6. The method of claim 5, wherein the selecting step (c)(i) further comprises a step of (c)(i)(1) choosing the area on the surface of the spinning data storage disc so as to include at least the damage caused to the surface during the head slap event.

7. A system for characterizing damage caused to a magnetic recording media on a surface of a data storage disc during a head slap event, the system comprising:
   an optical analyzer module comprising:
      a spindle, wherein the data storage disc is coupled to and spun on the spindle;
      at least one laser beam directed at the surface of the data storage disc; and
      at least one sensor operable to receive reflected light from the at least one laser beam reflecting from the surface of the data storage disc and sense changes in a direction of the reflected light;
   a data storage module operably coupled to the optical analyzer module for storing a plurality of data points generated by the optical analyzer module, the plurality of data points quantifying the changes in the direction of the at least one light beam; and
   a processing module coupled to the optical analyzer module and the data storage module operable to manipulate the plurality of data points to qualitatively and quantitatively represent the damage caused during the head slap event to the magnetic recording media on the surface of the data storage disc.

8. The system of claim 7, wherein the optical analyzer module further comprises a zoom module for focusing the at least one laser beam on a specified area on the surface of the data storage disc.

9. The system of claim 7, wherein the specified area is selected to include at least the damage caused during the head slap event.

10. The system of claim 7, wherein the processing module is a component of the optical analyzer module.

11. The system of claim 7, wherein the data storage module is a component of the optical analyzer module.

12. The system of claim 7, wherein the analyzer module is spaced apart from the surface of the data storage disc during analysis of the surface.

13. The system of claim 7, wherein the processing module generates at least one three-dimensional representation of the damage caused by the head slap event.

14. A disc damage analyzer comprising:
   an optical analyzer having a laser beam operably directed toward a magnetic recording media on a data storage disc and having a sensor to receive a plurality of light data points associated with reflected light from the laser beam reflecting from the surface of the data storage disc; and
   means for qualitatively and quantitatively characterizing the plurality of light data points to indicate damage caused by a head slap event.

15. The analyzer of claim 14, wherein the optical analyzer further comprises a zoom module for focusing the at least one laser beam on a specified area on the surface of the data storage disc.

16. The system of claim 15, wherein the specified area is selected to include at least the damage caused during the head slap event.

17. The system of claim 14, further comprising a processing module coupled to the optical analyzer, wherein the processing module generates at least one three-dimensional representation of the plurality of light data points.

18. A method of detecting damage to a magnetic recording media on a data storage disc caused by a head slap event in a disc drive, the method comprising steps of:
   (a) spinning a data storage disc having magnetic recording media on a surface of the storage disc, wherein the disc has previously been subjected to a head slap event in a disc drive;
   (b) scanning the surface of the spinning data storage disc using an optical analyzer laser beam;
   (c) sensing changes in a reflected light beam created by the laser beam reflecting from the surface of the spinning data storage disc;
   (d) acquiring a plurality of data points corresponding to the changes in the reflected light beam; and
   (e) characterizing the damage caused by the head slap event to the magnetic recording media on the surface of the spinning data storage disc based on the plurality of data points.

19. The method according to claim 18 wherein the characterizing step comprises steps of:

(e)(i) performing a qualitative analysis of the plurality of data points; and (e)(ii) performing a quantitative analysis of the plurality of data points.

20. The method of claim 19, wherein the characterizing step (e) further comprises a step of (e)(iii) determining a portion of a slider carried by an actuator arm in the disc drive that caused the damage to the surface of the spinning data storage disc from the qualitative and quantitative analyses.

21. A system for characterizing damage to a magnetic recording media on a surface of a magnetic data storage disc during a head slap event in a magnetic data storage disc drive, the system comprising:

an optical analyzer module comprising:

a spindle adapted to be coupled to a magnetic data storage disc and the disc spun on the spindle, wherein the disc has been subjected to a head slap event in a magnetic data storage disc drive;

at least one laser beam operable to be directed at a surface of the magnetic data storage disc when the disc is spun on the spindle; and at least one sensor operable to receive reflected light from the at least one laser beam reflecting from the surface of the magnetic data storage disc and sense changes in a direction of the reflected light;

a data storage module operably coupled to the optical analyzer module for storing a plurality of data points generated by the optical analyzer module, the plurality of data points quantifying the changes in the direction of the at least one laser beam; and a processing module coupled to the optical analyzer module and the data storage module operable to manipulate the plurality of data points to qualitatively and quantitatively represent damage caused during the head slap event to the magnetic recording media on the surface of the magnetic data storage disc.

* * * * *